United States Patent [19]

Cohen et al.

[11] Patent Number: 5,643,786

[45] Date of Patent: Jul. 1, 1997

[54] METHOD FOR ISOLATING DENDRITIC CELLS

[75] Inventors: Peter A. Cohen, Bethesda; Brian J. Czerniecki; Charles Carter, both of Gaithersburg; Daniel H. Fowler, Bethesda, all of Md.; Hyun Kim, Rochester, Minn.

[73] Assignee: The United States of America as represented by the Department of Health and Human Services, Washington, D.C.

[21] Appl. No.: 379,227

[22] Filed: Jan. 27, 1995

[51] Int. Cl.$^6$ .............................. C12N 5/00; C12N 5/06; A61K 33/06; A61K 35/14

[52] U.S. Cl. ..................... 435/325; 424/529; 424/530; 424/682; 435/375

[58] Field of Search ..................... 435/240.2; 424/529, 424/530, 682

[56] References Cited

U.S. PATENT DOCUMENTS 4,672,044  6/1987  Schieber .............................. 436/501

FOREIGN PATENT DOCUMENTS

| 0563485A1 | 3/1992 | European Pat. Off. . |
|---|---|---|
| WO9402156 | 2/1994 | WIPO . |

OTHER PUBLICATIONS

Kabel, P.J. et al., Immunobiol., vol. 179(4/5), pp. 395–411. Oct. 1989.

Ossevoort, M.A. et al., Dendritic Cells in Fundamental and Clinical Immunology, Edited by Kamperdijk et al., Plenum Press, New York, N.Y., pp. 185–189. Jul. 1993.

Rober, R.A. et al., Experimental Cell Research, vol. 190(2), pp. 185–194. Oct. 1990.

Gieseler, R.K. et al., European Journal of Cell Biology, vol. 54(1), pp. 171–181. 1991.

Chengzheng, L. et al., Chinese Medical Sciences Journal, vol. 6(1), pp. 18–23. Mar. 1991.

Spears, G.T. et al., "Oxidative Burst Capability of Human Monocyte Subsets Defined by High and Low HLA-DR Expression," Immunological Investigations, vol. 18(8), pp. 993–1005. 1989.

Knight, S, et al., Non-adherent, low-density cells from human peripheral blood contain dendritic cells and monocytes, both with veiled morphology, *Immunology*, 57:595–603, 1986.

De Boer, M. et al., Metabolic Comparison Between Basophils and other Leukocytes from Human Blood, *The Journal of Immunology*, 136:3447–3454, 1986.

Liu, C., et al., Phobol Myristate Acetate and Calcium Ionophore A23187 Modulate the . . . Mouse Dendritic Cells, *Chin Med Sci J.*, 6:18–23, 1991.

Liu, C., et al., *Biol Abstr* 93(11):AB–686.

Cohen PA, et al., Use of interleukin–7, interleukin–2, and interferon–gamma to propagate CD4+T cells in culture with maintained antigen specificity. *J. Immunother.* 14:242–252, 1993.

Esa AH, et al. Immunological heterogeneity of human monocyte subsets prepared by counterflow centrifugation elutriation. *Immunology* 59:95–99, 1986.

Freudenthal PS, et al., The distinct surface of human blood dendritic cells, as observed after an improved isolation method. *Proc. Natl. Acad. Sci.* 87:7698–7702, Oct. 1990.

Mehta-damani A, et al., Generation of antigen–specific CD8+ CTLs from naive precursors. *J. Immunol.* 153:996–1003, 1994.

Romani N, et al., Proliferating dendritic cell progenitors in human blood. *J. Exp. Med.* 180:83–93, Jul. 1994.

Thomas R, et al., Comparative accessory cell function of human peripheral blood dendritic cells and monocytes. *J. Immunol.* 151:6840–6852, Dec. 1993 No. 12.

Ossevoort, et al., A rapid isolation procedure for dendritic cells from mouse spleen by centrifugal elutriation. *J. Immunol. Methods* 155:101–111, 1992.

Peters, J. H. et al. "Pathobiology." vol. 59, 1991, pp. 122–126.

Primary Examiner—Michael G. Wityshyn
Assistant Examiner—Kristin Larson
Attorney, Agent, or Firm—Knobbe, Martens, Olson & Bear

[57] ABSTRACT

A method of isolating dendritic cells is described. This method involves elutriating peripheral blood samples in at least four flow rates from an elutriation rotor. Calcium ionophore is used to stimulate monocytes isolated during the process into dendritic cells. Treatments for diseases involving re-introduction of activated dentritic cells are also described.

7 Claims, No Drawings

METHOD FOR ISOLATING DENDRITIC CELLS

BACKGROUND OF THE INVENTION

Antigen presenting cells (APCs) are naturally occurring cells whose function is to present both "self" and "foreign" proteins (antigens) to the immune system. When antigens are effectively presented by APCs, they can activate T lymphocytes to recognize and fight infections as well as some types of cancer (Shimizu, J. et al. 1991 *J. Immunol.* 146:1708–1714; Zou, J. et al. 1992 *Cancer Immunol. Immunother.* 35:1–6; Takahashi, H. et al. 1993 *International Immunology* 5:849–857). Antigen-pulsed APCs have traditionally been prepared in one of two ways: (1) small peptide fragments, known as antigenic peptides, are "pulsed" directly onto the outside of the APCs (Mehta-Damani, A. et al. 1994 *J. Immunol.* 153:996–1003); or (2) APCs are incubated with whole proteins or protein particles which are then ingested by the APCs. These proteins are digested into small peptide fragments by the APC and eventually carried to and presented on the APC surface (Cohen, P. A. et al. 1994 *Cancer Res.* 54:1055–1058).

After APCs are prepared by one of the above methods, they can be injected back into a patient as a "vaccine," eventually reaching locations such as lymph nodes where they present the desired antigen to T lymphocytes (Inaba, K. et al. 1990 *J. Exp. Med.* 172:631–640 1990 [published erratum appears in *J. Exp. Med.* 1990 172(4):1275]). In another treatment, T lymphocytes are removed from a patient and stimulated to grow in culture by contact with the APCs (Cohen, P. A. et al. 1993 *J. Immunother.* 14:242–252). This latter approach can be used to propagate large numbers of "antigen specific" T lymphocytes which can be given to the patient as "adoptive immunotherapy."

An effective APC has several important properties: (1) it retains the peptide antigen on its cell surface long enough to present it to T lymphocytes; (2) it should process (ingest and digest) whole proteins or particles into peptide fragments as described above; (3) it can be activated to express additional "costimulatory" and adhesion molecules on its surface membrane which help T lymphocytes respond appropriately after encountering antigen on the APC surface.

Because effective antigen presentation requires a complicated system of cellular signals, researchers have concentrated on collecting human cells whose primary natural function is antigen processing and presentation. While a wide variety of cell types such as monocytes, macrophages, B cells and dendritic cells have a demonstrated ability to present antigen, extensive evidence indicates that the dendritic cell (DC) is nature's most potent antigen-presenting cell. DCs can express all of the necessary costimulatory and presentation molecules with great flexibility. In addition, dendritic cells' only known function is antigen presentation. While other types of APCs are capable of resensitizing T lymphocytes to previously encountered antigens (so-called "recall" antigens), DCs are thought to be most responsible primary sensitization of T lymphocytes (Croft, M. et al. 1994 *J. Immunol.* 152:2675–2685).

DCs are derived from "myeloid precursor" cells in the bone marrow which also give rise to monocytes and macrophages (Thomas, R. et al. 1994 *J. Immunol.* 153:4016–4028). It is also possible that monocytes are themselves the immediate precursors of both DCs and macrophages. As support for this theory, researchers have found that monocytes are capable of developing into cells morphologically and immunophenotypically identical to either DCs or macrophages in culture. This finding indicates that lymphocytes which share the same bone marrow precursor are relatively uncommitted to a particular differentiation pathway for at least some portion of their development (Peters, J. H. et al. 1991 *Pathobiology* 59:122–126).

Because DCs are derived from the bone marrow, they must travel through the blood until they reach their destination organs. These target organs include virtually every organ in the body. Due to this essential transit through the blood, the blood itself is the richest available source of DCs in the human body. It has been estimated that 1–3% of all mononuclear blood cells are precommitted DCs (Thomas, R. et al. 1993 *J. Immunol.* 151:6840–6852). The 10–15% of peripheral blood mononuclear cells which are monocytes may also, at least in part, have the potential to differentiate into DCs (Peters, J. H. et al. 1991 *Pathobiology* 59:122–126).

A number of strategies have been developed by others to isolate and purify human DCs from peripheral blood. The two fundamental approaches involve (1) isolating bone marrow precursor cells (CD34$^+$) from blood and stimulating them to differentiate into DCs; or (2) collecting the precommitted DCs from peripheral blood. While the first approach is of great theoretic interest, the patient must unadvantageously be treated with cytokines such as GM-CSF to boost the number of circulating CD34$^+$ stem cells in the peripheral blood. Moreover, the procedures necessary to generate large numbers of DCs are costly and lengthy, and the function of DCs obtained in this fashion has not yet been proved adequate for many applications (Romani, N. et al. 1994 *J. Exp. Med.* 180:83–93). In addition, exposing DCs in culture to foreign proteins such as fetal calf serum can cause them to preferentially present these unwanted antigens.

The second approach for isolating DCs is to collect the relatively large numbers of precommitted DCs already circulating in the blood. Previous techniques for preparing mature DCs from human peripheral blood have involved combinations of physical procedures such as metrizamide gradients and adherence/nonadherence steps (Freudenthal, P. S. et al. 1990 *Proc. Natl. Acad. Sci.* 87:7698–7702); Percoll gradient separations (Mehta-Damani, et al. 1994 *J. Immunol.* 153:996–1003); and fluorescence activated cell sorting techniques (Thomas, R. et al. 1993 *J. Immunol.* 151:6840–6852). All of these methods are uniformly plagued by small final DC yields, quality control problems and/or probable functional alterations of the DCs due to physical trauma and the extended period of time required to complete these procedures.

One technique for separating large numbers of cells from one another is known as countercurrent centrifugal elutriation (CCE). In this technique, cells are subject to simultaneous centrifugation and a washout stream of buffer which is constantly increasing in flow rate. The constantly increasing countercurrent flow of buffer leads to fractional cell separations that are largely based on cell size.

It was demonstrated over ten years ago that when human blood mononuclear cells were separated by countercurrent centrifugal elutriation (CCE) into two basic fractions, then called "lymphocyte fraction" and "monocyte fraction," that the "monocyte" fraction possessed the ability to present a recall antigen, tetanus toxoid, to the "lymphocyte" fraction (Esa, A. H. et al. 1986 *Immunology* 59:95–99). However, these investigators did not attempt to use elutriation to specifically isolate dendritic cells from the peripheral blood. Additionally, these investigators did not question whether the monocyte fraction could sensitize T lymphocytes to antigens never previously encountered ("primary in vitro sensitization").

In experiments performed between 1992 and 1994, we performed CCE in the "traditional" manner. As was known, CCE separates cells by their size. Cell fractions were taken from the elutriation rotor at specific buffer flow rates, while the rotor spins at a constant rate. During the procedure, the buffer is constantly increasing in flow rate. In these previous experiments, we elutriated cell fractions from the rotor at a constant centrifugal speed of 3000 rpm. The following fractions were isolated in the traditional manner.

- a "140" fraction (traditional lymphocyte fraction) was collected and used as a source of lymphocytes. This fraction was elutriated at a buffer flow rate of 140 cc/min.
- a "150" fraction, known as "intermediate" was discarded as is traditionally customary. This fraction was elutriated at a buffer flow rate of 150 cc/min.
- a "rotor off (R/0)" fraction (traditional "monocyte" fraction) was collected and used as a source of APCs. This fraction was collected by eluting the cells remaining in the initial sample after the rotor has stopped.

Following elutriation, each fraction was cryopreserved in 10% DMSO so it could be stored and thawed for use at later times. However, as with prior attempts to isolate dendritic cells from other blood cells, this procedure did not provide good yields of dendritic cells. In a typical experiment, we only found a 2–3 fold enrichment of dendritic cells. Typically, we could obtain about $1 \times 10^7$ dendritic cells from one isolation procedure.

Other cell isolation techniques have additionally used fluorescent activator cell sorting (FACS) to subselect DCs from other peripheral blood cells (Thomas, R. et al. 1994 *J. Immunol.* 153:4016–4028; Thomas, R. et al. 1993 *J. Immunol.* 151:6840–6852). However, all of these methods have inherent disadvantages. The final yields are relatively small, indicating losses of most of the initial DCs during inefficient and potentially traumatic purification processes.

Further, these methods are extremely time-consuming and prone to quality control problems. During these procedures purified DCs have been found to no longer be able to process antigen effectively after undergoing several days of mechanical purifications and/or FACS manipulations. In addition, monocytes, themselves a potential precursor of DCs, are lost in the purification process since they are part of the discarded 150 fraction. Mouse studies of dendritic cell isolation have demonstrated that enrichment methods which require several hours rather than days result in a more fully functional DC collection (Girolomoni, G. 1990 *J. Immunol.* 145:2820–2826).

Some investigators have shown rapid methods of isolating dendritic cells from mouse spleen cells by centrifugal elutriation followed by FACS analysis (Ossevoort, M. A. et al. 1992 *J. Immunol. Methods* 155(1):101–11). However, such rapid collection techniques have not been used to isolate dendritic cells from peripheral blood. In addition, a large number of the monocytes that co-migrate upon countercurrent centrifugal elutriation are wasted because there is no reliable method of isolating immunologically activated dendritic cells from monocytes. Therefore, a need exists for a method of isolating dendritic cells that results in large yields, but is quick and efficient. Further, a method of converting monocytes to dendritic cells needs to be developed to increase the yield of dendritic cells isolated from the peripheral blood.

SUMMARY OF THE INVENTION

One embodiment of the present invention is a method of isolating dendritic cells from the peripheral blood of a mammal, comprising the following steps;

a) providing a white blood cell fraction obtained from a mammalian source;

b) separating the white blood cell fraction into four or more subfractions by countercurrent centrifugal elutriation;

c) identifying the dendritic cell-enriched fraction from step (b); and d) collecting the enriched fraction of step (c).

Another embodiment of the present invention is a method of producing dendritic cells from the white blood cell fraction of a mammal, comprising the following steps:

a) providing a white blood cell fraction obtained from a mammalian source;

b) separating the white blood cell fraction of step (a) into four or more subfractions by countercurrent centrifugal elutriation;

c) stimulating conversion of monocytes in one or more fractions from step (b) to dendritic cells by contacting the cells with calcium ionophore;

d) identifying the denaritic cell-enriched fraction from step (c); and e) collecting the enriched fraction of step (d).

Still another aspect of the present invention is a method of increasing the immune response of a mammal to a disease-carrying agent, comprising the steps of:

a) providing a white blood cell fraction obtained from said mammal;

b) separating the white blood cell fraction of step (a) into four or more subfractions by countercurrent centrifugal elutriation;

c) stimulating conversion of monocytes in one or more fractions from step (b) to dendritic cells by contacting the cells with calcium ionophore;

d) incubating said dendritic cells in the presence of an antigen specific for said disease-carrying agent; and e) reintroducing said dendritic cells into the mammal.

DETAILED DESCRIPTION

The present invention is a method for rapidly isolating dendritic cells from peripheral blood. The method involves use of leukapheresis to initially isolate neutrophil-depleted, platelet-rich blood cells from a donor. Leukapheresis involves continuously extracorporealizing blood from a donor using laminar flow properties to separate mononuclear (white) cells and platelets from red cells and plasma. The unneeded red cells and plasma are returned to the patient during the leukapheresis procedure. With this technique, the white cells and platelets are selectively removed from many liters of a donor's blood over a several hour period without harming the donor.

During the development of our method, we found that a rinse of EDTA-free, $Ca^{++}/Mg^{++}$-free citrate buffer following leukapheresis dramatically increased the final yield of dendritic cells. We believe that this is due to rinsing away of contaminating proteins, cell fragments and calcium from the leukaphereis procedure. While the use of a citrate buffer is preferred, other cold buffers known in the art could be substituted without departing from the spirit of this feature of the invention.

Following a rinse with a citrate buffer, we perform countercurrent centrifugal elutriation (CCE) on the enriched collection of blood cells from leukapheresis. CCE more specifically isolates monocytes and dendritic cells from other white blood cells. As explained above, countercurrent centrifugal elutriation is a technique whereby the cells are subject to simultaneous centrifugation and a washout stream of buffer which is constantly increasing in flow rate. The constantly increasing countercurrent flow of buffer leads to fractional cell separations that are largely based on cell size. The present invention exploits the selection mechanism of CCE in conjunction with leukapheresis to result in high purity dendritic cell preparations.

During our procedures, it became apparent that the majority of peripheral blood dendritic cells in a sample could be consistently collected without neutrophil contamination in a newly defined "Antigen Presenting Cell Fraction". This fraction consisted of 92–95% monocytes and 5–8% dendritic cells, with the absolute number of dendritic cells being the vast majority of those present in the patient's peripheral blood sample. On a typical pheresis/elutriation collection, this fraction would represent a yield of $1–1.5 \times 10^8$ partially purified dendritic cells, at least ten fold greater numbers than any other published method (Freudenthal, P. S. et al. 1990 Proc. Natl. Acad. Sci. 87:7698–7702; Romani, N. et al. 1994 J. Exp. Med. 180:83–93; Thomas, R. et al. 1993 J. Immunol. 151:6840–6852; Mehta-Damani, A. et al. 1994 J. Immunol. 153:996–1003). While this large dendritic cell subpopulation could then be separated from the monocytes in a number of ways, including a FACS sort, the advisability of such a separation was unclear. Some investigators had reported that monocytes themselves could develop dendritic morphology and function in the presence of certain cell culture media or cytokines, notably IL-4 (Peters, J. H., et al. 1991 Pathobiology 59:122–126).

Therefore, we decided to formulate an additional method of developing a reliable means to convert the bulk monocyte population to a cellular phenotype indistinguishable from activated dendritic cells. As part of this investigation, we discovered that calcium ionophore could be used to convert isolated monocytes into functional dendritic cells. This converted monocyte population, once added to the isolated dendritic cell population, could provide a typical total dendritic cell yield of $1–1.5 \times 10^9$ cells, which was 100–1000 fold greater than any other published method. This feature of the invention is discussed in greater detail below.

Because there is currently no surface antigen marker available for positive identification of human DCs (as opposed to a number of antigens, such as 33D1, which are available for mouse DC (Ossevoort et al., supra)), we needed to develop a FACS technique that would detect and measure DC subpopulations present in each elutriation fraction from fresh peripheral blood. This involved simultaneously staining the cells with a cocktail of fluorescent antibodies of one color (e.g., fluorescein) to markers that are absent from DCs (e.g. CD3, CD20, CD56 and CD14) and additional antibodies of a different color (e.g. phycoerythrin) that are known to be present on, but not unique to dendritic cells (HLA-DR, B7.2, CD13/33, etc.) This negative cocktail plus positive marker approach enabled demonstration of a unique subpopulation with uniform forward and side scatter properties (ie, size and organelle content) which correlated to those expected of DCs.

Detailed Explanation of Each Method Step

Leukapheresis

The current patent application discloses a method for rapidly isolating dendritic cells from peripheral blood. In this method, a patient initially undergoes leukapheresis (LP) to isolate white blood cells from other blood cells. Leukapheresis involves extracorporealizing blood continuously from the human donor or patient, using laminar flow properties to separate mononuclear (white) cells and platelets from red cells and plasma. The red cells and plasma were then returned back into the patient. In this fashion, the white cells and platelets can be selectively removed from many liters of patient or donor blood over a several hour period without harming the patient.

Countercurrent Centrifugal Elutriation

The bulk enriched collection of white cells and platelets from leukapheresis was then further fractionated by countercurrent centrifugal elutriation (CCE) (Abrahamsen T. G. et al. 1991 J. Clin. Apheresis. 6:48–53). Cell samples are placed in a special elutriation rotor. The rotor is then spun at a constant speed of, for example, 3000 rpm. Once the rotor has reached the desired speed, pressurized air is used to control the flow rate of cells. Cells in the elutriator are subjected to simultaneous centrifugation and a washout stream of buffer which is constantly increasing in flow rate. This results in fractional cell separations based largely but not exclusively on differences in cell size.

Our analyses revealed that a subpopulation of dendritic cells was present in all three "traditional" elutriation fractions, though in varying numbers from one collection to another. The dendritic subpopulation constituted from one to over 2% of the predominantly lymphocyte fraction; 5–15% of the intermediate fraction, and 2–5% of the monocyte fraction. In addition, a high degree of neutrophil contamination (up to ⅔ of the total cells) was found exclusively in the traditional monocyte fraction. Such neutrophil contamination was more frequently seen during collection from cancer patients than from normal donors. Therefore, following the "traditional" method of elutriation, many dendritic cells were lost in the lymphocyte fraction and, those dendritic cells present in the monocyte fraction were often unusable due to neutrophil contamination.

During our investigations we found, as expected, that cells in the traditional monocyte APC fraction inefficiently presented antigen in several regards:

While generally reliable for restimulating T-lymphocytes already sensitized to "recall" antigens such as tetanus, they were much less efficient in enabling primary sensitization to novel antigens, as well as to tumor antigens in general.

FACS-guided separations indicated that whatever ability the monocyte fraction had to sensitize T lymphocytes to novel antigens was attributable to a small dendritic cell subpopulation.

The monocytes in the monocyte fraction consistently failed to upregulate important costimulatory molecules such as B7.1 when they were cultured in the presence of a variety of test antigens. In contrast, the elutriated dendritic cell subpopulation did upregulate costimulatory molecules in the presence of certain antigens, and such upregulation was accompanied by improved antigen presentation. However, upregulation of costimulatory molecules in the dendritic cell subpopulation did not occur in the presence of most tested antigens, including tumor antigens.

For these reasons, we attempted to improve on the previous dendritic cell isolation methods. The following is an overview of the method for isolating dendritic cells. Leukapheresis (LP) was driven by "neutrophil-depleting, platelet-rich" software such as Procedure 8 Modification available on the Fenwal™ CS3000 pheresis apparatus (Fenwal, Inc. Round Lake, Ill.). While this product is a preferred software and hardware package that can be used to provide the desired leukapheresis properties, one of ordinary skill in the art will recognize that any similar product that can be programmed to be neutrophil-depleting and platelet-rich will also work in the present invention.

In addition, however, the elutriation (CCE) procedure was modified so that we could elutriate cell subpopulations at a new set of intermediate fractions. This new procedure involved taking additional fractions with a constant rotor speed of 3000 rpm while the buffer flow rate was increasing. Instead of only taking fractions at the traditional flow rates of 140 and 150 cc/min, we obtained cell fractions at 120, 140, 150, 160, 170, 180, 190 and 200 cc/min. Previous investigators had believed that isolating fractions at the higher flow rates would not increase the number of isolated dendritic cells.

We discovered that monocytes and dendritic cells were collectable without neutrophil contamination in newly defined "intermediate" fractions from 150 to 200 (see Table 1). After these new intermediate fractions, a final rotor-off (R/O) fraction was DC poor, monocyte variable, and often highly contaminated by neutrophils. The R/O fraction was easily Coulter analyzed and discarded if contaminated.

When the R/O fraction was highly contaminated, the immediately preceding fractions (200 and sometimes 190) also had a high likelihood of neutrophil contamination. The neutrophil poor fractions—always 150 to 180 and often also 90—were DC enriched and monocyte-rich, and were therefore pooled as the "APC" collection. This method of using newly defined intermediate fractions thus enabled easy identification and elimination of neutrophil contaminated fractions, and provided a highly enriched source of DCs.

TABLE 1

Comparison of CCE Fractions in Traditional and New Method

| Fraction | TRADITIONAL METHOD | Fraction | NEW METHOD |
|---|---|---|---|
| | | 120* | - Essentially pure lymphocytes<br>- Non-lymphocyte contaminants can be reduced by extra washes before elutriation and by not overloading the elutriator (maximum 4–5 × $10^9$ cells/run)<br>- This fraction of essentially contain less than 0.5% identifiable dendritic cells |
| 140 | - Lymphocytes plus contaminant non- lymphocytes from overloading<br>- Up to 2% of the fraction by FACS analysis is DCs<br>- In absolute numbers, this fraction can contain 25–45% of the total peripheral blood DC concentration in the peripheral blood. | 140* | - Large fraction of essentially pure lymphocytes<br>- Typically contains less than 0.5% identifiable dendritic cells |
| 150 | - Variable discarded fraction, including DCs<br>- By FACS analysis, between 15–28% of this fraction are DCs. | 150** | - Lymphocytes plus first DC-rich fraction<br>- DCs –5–10% of this fraction |
| | | 160** | - DC-richest fraction, rest monocytes<br>- DCs –15–25% of this fraction |
| | | 170** | - DC-richest fraction, rest monocytes<br>- DCs –15–25% of this fraction |
| | | 180** | - DC-rich fraction, rest monocytes<br>- DCs –10–15% of this fraction |
| | | 190** | - Monocyte fraction, variably DC-rich<br>- DCs –5–10% of this fraction |
| | | 200 | - Monocyte fraction. rarely DC-rich<br>- Sometimes contaminated by neutrophils<br>- DCs less than 5% of this fraction |
| R/O | Monocyte fraction less than 5% of total DC population, often largely neutrophil contaminated | R/O | - Monocute fraction<br>- Sometimes neutrophil contamination<br>- DCs typically less than 2% of fraction |

*Usually pooled as "lymphocyte fraction"
**Usually pooled as "APC" fraction

As shown in Table 1, traditional CCE methods resulted in loss of DCs into the earlier lymphocyte (140) and intermediate (150) fraction despite the fact that DCs are larger in size than lymphocytes and technically should not be eluted in great numbers until after the 150 fraction. This is one reason why this problem has persisted in the art until our improvement. Because the traditional lymphocyte (140) fraction constituted over 5/7 of the total elutriated cells products, a very small percentage of dendritic cells in the fraction would constitute between 25–45% of the total dendritic cell population in the peripheral blood.

We believe that specific factors contributed to premature dumping of DCs in the elutriation process, including carryover of plasma proteins from LP into CCE, apparently altering cell sedimentation rates. In addition, it seems that in cancer patients carryover tumor-related blood proteins from LP into CCE. Finally, addition of certain chemicals such as EDTA to the buffer during elutriation appears to negatively effect isolation efficiencies. To prevent these factors from impairing elutriation, we have introduced a washing step: following LP (leukapheresis), the cells are centrifuged, resuspended in a cold citrate buffer solution, and washed thoroughly to reduce the carryover of plasma, tumor-related proteins, calcium, etc. Subsequently, the cells are resuspended in EDTA-free, $Ca^{++}/Mg^{++}$-free Hanks' balanced salt solution (HBSS) before being subjected to elutriation. With this corrected technique, a small initial enrichment of DCs begins to appear at fraction 150 with peak DC elutriation reliably occurring between fractions 155 and 180, and is largely completed by fraction 190. This improvement would not have been expected upon addition of a washing step following leukapheresis.

Maintaining Elutriated Cells on Ice

We have also identified that there is a major loss of cells during elutriation due to adhesion of cells to plastic bags during collection. This is probably exacerbated when the cells are kept in the bag for extended periods prior to processing. We have ascertained that this adhesion is temperature dependent, and lowering the temperature during collection typically doubles the yield of the monocyte/DC fractions. Elutriation has therefore been modified to reduce the collection temperature to 4° C. by keeping the collection bags on ice and partially prefilling them with chilled buffer. This markedly improves yields and does not impair function. Since cells are normally cryopreserved after elutriation, they are maintained at this low temperature until the cryopreservation process.

FACS Analysis to Monitor Quality of Elutriation

Quality control of APC collection and confirmation of their successful activation in culture is dependent upon a simultaneous multi-color FACS analysis technique we have developed to monitor both monocytes and the dendritic cell subpopulation as well as possible contaminant T lymphocytes. It is based upon the fact that DCs do not express the following markers: CD3 (T cell); CD14 (monocyte); CD16, 56,57 (NK/LAK cells); CD19, 20 (B cells). At the same time, DCs do express large quantities of HLA-DR, significant HLA-DQ and B7.2 (but little or no B7.1) at the time they are circulating in the blood (in addition they express Leu M7 and M9, myeloid markers which are also expressed by monocytes and neutrophils). When combined with a third color reagent for analysis of dead cells, propridium iodide (PI), it is possible to make positive identification of all cell subpopulations (see table 2):

TABLE 2

FACS analysis of fresh perish cell subpopulations

| | Color #1 Cocktail 3/14/16/19/20/56/57 | Color #2 | Color #3 |
|---|---|---|---|
| Live Dendritic cells | Negative | Positive | Negative |
| Live Monocytes | Positive | Positive | Negative |
| Live Neutrophils | Negative | Negative | Negative |
| Dead cells | Variable | Variable | Variable |

Additional markers can be substituted for additional analysis:

Color #1: CD3 alone, CD14 alone, etc; Leu M7 or Leu M9; anti-Class I, etc

Color #2: HLA-Dq, B7.1, B7.2, CD25 (IL2r), ICAM, LFA-3, etc.

The goal of FACS analysis at the time of collection is to confirm that the DCs are enriched in the expected fractions (150–190), to monitor neutrophil contamination, and to make sure that appropriate markers are expressed. This rapid bulk collection of enriched DCs from human peripheral blood, suitable for clinical applications, is absolutely dependent on the analytic FACS technique described above for quality control. If need be, mature DCs can be immediately separated from monocytes at this point by fluorescent sorting for "cocktail negative" cells. We do not, however, routinely separate DCs from monocytes because, as will be detailed below, the monocytes themselves are still capable of differentiating into DCs or functional DC-like cells in culture.

Once collected, the DC rich/monocyte APC fractions (usually 150 through 190) can be pooled and cryopreserved for future use, or immediately placed in short term culture. We have defined new and essential culture conditions for optimal activation of and antigen processing by these APCs. The goals are:

to enable optimal processing of added proteins or uptake of pulsed peptides, optimal and controlled upregulation of essential costimulatory and presenting molecules on DCs such as B7.1, B7.2 and HLA-DR and HLA-DQ, conversion of the large monocyte population to an activated DC-like phenotype so that they also can participate in effective antigen processing and presentation.

Use of Calcium Ionophore to Convert Monocytes into Activated Dendritic Cells

We have discovered that a new and useful method exists for upregulating (activating) dendritic cells and converting monocytes to an activated dendritic cell phenotype. This method involves our discovery that addition of calcium ionophore to the culture media converts monocytes into activated dendritic cells. Adding the calcium ionophore A23187, for example, at the beginning of a 24–48 hr culture period resulted in uniform activation and dendritic cell phenotypic conversion of the pooled "monocyte plus DC" fractions: characteristically, the activated population becomes uniformly CD14 (Leu M3) negative, and upregulates HLA-DR, HLA-DQ, ICAM-1, B7.1, and B7.2. Furthermore, this activated bulk population functions as well on a small numbers basis as a further purified subpopulation of dendritic cells.

We have found that no added other reagents, such as cytokines, were as effective as calcium ionophore in upregulating the dendritic cell subpopulation, and no other studied reagents were effective at all in converting monocytes to an activated dendritic cell phenotype. However, certain specific combination(s) of cytokines have been used successfully to amplify (or partially substitute) for the activation/conversion achieved with calcium ionophore: these cytokines include but are not limited to rhGM-CSF, rhIL-2, rhIL-4 and rhIL-12. Each cytokine when given alone is inadequate for optimal upregulation. The process for isolating dendric cells is summarized in Table 3.

EXAMPLE 1

Isolation of Dendritic Cells from Human Normal and Colon Cancer Patients

Two patients were hooked up to Fenwal™ CS-3000 leukapheresis apparatus' running a Procedure 8 modification software program. Patient #1 had been previously diagnosed with colon cancer, and Patient #2 was a normal control. The Fenwal™ apparatus was configured to isolate a sample of neutrophil-depleted, platelet-rich cells from each patients' peripheral blood. After 3–5 hours of leukaphereis, the isolated blood cells from each patient were quickly spun down in a centrifuge and then rinsed in citrate buffer to remove any excess plasma, tumor related proteins or calcium.

Following the citrate buffer rinse, the cells were resuspended in EDTA-free, $Ca^{++}/Mg^{++}$-free HBSS. The isolated cells from each patient were then subject to elutriation on a Beckman™ JE-6B elutriation rotor. Once reaching a speed of 3000 rpm, $5 \times 10^9$ cells were elutriated by pressurized air at buffer flow rates of 120, 140, 150, 160, 170, 180, 190 and 200 cc/minute.

Each fraction from both patients was immediately placed on ice to prevent cell adherence to the plastic walls of the collection vials. We coulter counted each of the fractions and discarded the r/o fraction because it had greater than a 10% contamination of neutrophils. The 150, 160, 170, 180 and 190 cc/min fractions from Patient #1 and Patient #2 were pooled then subject to calcium ionophore. The pooled fractions from each patient were divided in half, with one half being activated by 500 ng of calcium ionophore A23187 (Sigma), and one half being inactivated. From our previous experiments, we expected that the calcium ionophore treated cells would have a much higher number of dendritic cells due to conversion of monocytes to DCs. Prior to FACS analysis, we activated Patient #1's pooled fractions by incubating both the untreated and calcium ionophore treated cells for 40 hours in the presence of an autologous tumor cell lysate (the patient's own tumor cells). Similarly, we activated Patient #2's pooled fractions by incubating both the untreated and calcium ionophore treated cells in the presence of keyhole limpet hemocyanin (KLH) for 40 hours.

In each of the FACS plots, the vertical (Y) axis showed staining for a cocktail of CD3, CD14, CD20 and CD56 surface antigens. The vast majority of cells stained in the pooled fractions were expected to be CD14+ (ie: monocytes). The horizontal (X) axis of the FACS plot illustrated staining for DR, B7.1 or B72 surface antigens. Our results of the FACS analysis were as follows:

Normal Donor (NO calcium ionophore treatment)

The vast majority of cells in this fraction remained CD14+ indicating that they remained monocytes. However, a subset of the cocktail negative (dendritic) cells showed marked upregulation of HLA-DR, B7.1 and B7.2.

Normal Donor (WITH calcium ionophore treatment)

The vast majority of these cells was now cocktail negative (dendritic) and markedly upregulated for HLA-DR, B7.1 and B7.2. This matched a dendritic cell phenotype indicating that a number of the monocytes had converted over to dendritic cells.

Colon Cancer Pt. (NO calcium ionophore treatment)

The vast majority of these cells remained cocktail positive, with a subset of negative (dendritic) cells showing modest upregulation of HLA-DR, and B7.2, but only a little upregulation of B7.1.

Colon Cancer Pt. (WITH calcium ionophore treatment)

The vast majority of cells were now converted to cocktail negative indicating that they had become dendritic cells. There was a marked upregulation of HLA-DR and B7.2. There was also a substantial but less uniform upregulation of B7.1.

This experiment demonstrated that calcium ionophore treatment increased the yield of activated dendritic cells by many times over untreated cell fractions. We are able to obtain up to $1 \times 10^9$ dendritic cells using this technique from a single peripheral blood leukapheresis. This is an increase of more than 100 fold over previous dendritic cell isolation methods. The use of calcium ionophore to convert monocytes to dendritic cells can therefore provide a very valuable tool for investigators and clinicians that require large numbers of dendritic cells for a clinical treatment.

As discussed above, populations of activated dendritic cells isolated by the method of the present invention can be easily reintroduced into a patient to help augment a weak or dysfunctional immune system.

EXAMPLE 2

Treatment of Cancer in a Patient with Autologous Dendritic Cells

Dendritic cell enriched fractions are isolated from a patient in need of treatment for prostate cancer by leukapheresis, citrate buffer rinse and CCE as described above in Example 1. After pooling the 150, 160, 170 and 180 cc/min elutriation fractions, they are subject to activation by 500 ng calcium ionophore A23187. The pooled fractions are then incubated for 40 hours with a prostate tumor cell lysate from prostate cancer cells previously obtained from a biopsy of the patient. This incubation activates the dendritic cell population to present prostate tumor cell antigens.

After incubation in the presence of the prostate tumor antigens, the cells are reintroduced intravenously into the patient. Three weeks later, a reduction in the size of the prostate tumor is noticed due to activation of the patient's immune system via the introduced, activated dendritic cells.

Although this is one example of a possible antigen that could be used in the present technique, one of ordinary skill in the art will recognize that other similar antigens could also function effectively. For example, dendritic cells can be challenged with antigens from the surface of HIV-1, or other disease-carrying agent and then reintroduced into a patient that has AIDS. Other types of disease-carrying agents, such as cancer cells of the breast, brain, liver or stomach are also anticipated to function effectively to activate dendritic cells to present tumor antigens in the methods of the present invention. In this manner, the physician can stimulate an anti-cancer antigen response in vitro, and then reintroduce the patients own antigen-presenting dendritic cells as a method of increasing the immune response to the tumor cells.

Preferred features of the present invention have been described above. However, the true scope of the invention is not limited to only those embodiments illustrated in the Detailed Description, but should only be limited by the scope of the following claims.

TABLE 3

Summary Of Steps for Isolating Dendritic Cells.

1. Patient or donor leukapheresis (LP) using platelet-rich, neutrophil-poor collection mode (e.g., on CS3000 using neutrophil-poor software program)
2. LP collected cells centrifuged, washed in citrate buffer to remove interfering proteins, room temperature. Resuspend cells in HBSS without $CA^{++}/Mg^{++}$ or EDTA
3. Washed cell aliquot loaded (conservative cell load) at room temperature onto elutriator (CCE). Folloiwng fractions collected: 120, 140, 150, 180, 190, 200, Rotor off (R/O)
4. Fractions collected immediately on ice to prevent cell adherence

TABLE 3-continued

Summary Of Steps for Isolating Dendritic Cells.

5. Coulter counter histogram used for rapid analysis of neutrophil contamination in later fractions; discard R/O, etc., if contamination >10%
6. Pool and/or cryopreserve appropriate fractions (120 + 140 pooled as a lymphocyte fraction unless 120 contaminated from overload, in which case 140 alone used as lymphocyte fraction; 150 + 180 + 190 usually pooled as APC (monocyte + DC) frction; however, 160 and 170 fraction can be used alone as "highly DC" enriched fractions.
7. Triple color FACS analysis for quality control of 1–6 step collection.
8. APC fraction placed in short term culture (either fresh cells or thawed cryopreserved cells) to upregulate necessary APC molecules including B7 .1 and HLA-DQ. Calcium ionophore typically used to activate DC subpopulation and convert bulk monocyte population over to activated DC phenotype. Specific recombinant cytokine combinations added to culture in some instances (e.g., rhIL-12, rhGM-CSF, rhIL-4 and rhIL-2).
9. Cultured/activated, antigen pulsed APCs harvested using $Ca^{++}/Mg^{++}$ free medium (HBSS or pbs) with collection into ice cold buffer in tubes kept on ice.
10 Triple color FACS analysis for quality control of APC activation
11 Use activated, antigen pulsed APCs to stimulate growth of T lymphocytes in culture or reinject into patient as a "vaccine."

We claim:

1. A method for inducing monocytes to exhibit the phenotype of activated myeloid dendritic cells, comprising contacting said monocytes with an amount of a calcium ionophore effective to cause the contacted cells to downregulate CD14 and to upregulate HLA-DR, HLA-DQ, ICAM-1, and B7.2.

2. A method for producing cells having the phenotype of activated myeloid dendritic cells from mammalian monocyte blood cells, comprising:

(a) providing a cell fraction comprising monocytes from a mammalian blood sample;

(b) isolating at least one monocyte-enriched subfraction of the cell fraction of step (a);

(c) contacting the cells in the subfraction of step (b) with an amount of a calcium ionophore effective to induce said contacted cells to downregulate CD14 and to upregulate HLA-DR, HLA-DQ, ICAM-1, and B7.2; and (d) collecting the contacted cells of step (c).

3. The method of claim 2 wherein the monocyte-enriched subfraction of step (b) is isolated by countercurrent elutriation.

4. The method of claim 3 further comprising the step of identifying the cells induced to downregulate CD14 and to upregulate HLA-DR, HLA-DQ, ICAM-1, and B7.2 in step (c) by fluorescence-activated cell sorting.

5. The method of claim 2 wherein step (c) further comprises contacting the subfraction with a cytokine.

6. The method of claim 5 wherein the cytokine is selected from the group consisting of rhIL-12, rhGm-CSF, rhIL-4 and rhIL-2.

7. The method of claim 2, wherein the cell fraction of step (a) is obtained by leukapheresis.

* * * * *

UNITED STATES PATENT AND TRADEMARK OFFICE
CERTIFICATE OF CORRECTION

PATENT NO.   : 5,643,786                          Page 1 of 1
DATED        : July 1, 1997
INVENTOR(S)  : Peter A. Cohen et al.

It is certified that error appears in the above-identified patent and that said Letters Patent is hereby corrected as shown below:

Column 14,
Line 11, insert -- then -- before "contacting"

Signed and Sealed this

Twenty-fifth Day of November, 2003

JAMES E. ROGAN
*Director of the United States Patent and Trademark Office*